(12) United States Patent
Chodkowski et al.

(10) Patent No.: US 10,183,137 B2
(45) Date of Patent: Jan. 22, 2019

(54) RESPIRATORY INTERFACE DEVICE CUSTOMIZATION UTILIZING A GENERIC CUSHION TEMPLATE

(71) Applicant: KONINKLIJKE PHILIPS N.V., Eindhoven (NL)

(72) Inventors: Lauren Patricia Chodkowski, Pittsburgh, PA (US); Robert William Baiko, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 642 days.

(21) Appl. No.: 14/651,888

(22) PCT Filed: Dec. 5, 2013

(86) PCT No.: PCT/IB2013/060658
§ 371 (c)(1),
(2) Date: Jun. 12, 2015

(87) PCT Pub. No.: WO2014/091370
PCT Pub. Date: Jun. 19, 2014

(65) Prior Publication Data
US 2015/0314096 A1 Nov. 5, 2015

Related U.S. Application Data

(60) Provisional application No. 61/737,316, filed on Dec. 14, 2012.

(51) Int. Cl.
*A61M 16/06* (2006.01)
(52) U.S. Cl.
CPC ........ *A61M 16/06* (2013.01); *A61M 16/0622* (2014.02); *A61M 2016/0661* (2013.01);
(Continued)

(58) Field of Classification Search
CPC .......... A61M 2016/0661; A61M 16/06; A61M 16/0605; A61M 16/0611; A61M 16/0616;
(Continued)

(56) References Cited

U.S. PATENT DOCUMENTS 5,832,918 A * 11/1998 Pantino ............. A61M 16/0683
128/200.24
6,196,223 B1 * 3/2001 Belfer ................ A41D 13/1176
128/205.25

(Continued)

FOREIGN PATENT DOCUMENTS

DE 10138416 A1 2/2003
DE 102005042911 A1 3/2007
(Continued)

OTHER PUBLICATIONS

Machine translation of EP 1116492 A2.*
Machine translation of FR 2824739 A1.*
By-hand translation of EP 1116492 A2.*

*Primary Examiner* — (Jackie) Tan-Uyen T Ho
*Assistant Examiner* — Joseph D Boecker
(74) *Attorney, Agent, or Firm* — Michael W. Haas

(57) ABSTRACT

A respiratory interface device is provided. The respiratory interface device includes a cushion structured to be coupled to a faceplate that includes a peripheral end and a coupling assembly. The faceplate peripheral end includes a formable material and a portion of faceplate peripheral end is a customized contoured end. Cushion is coupled to faceplate adjacent faceplate customized contoured end, cushion conforming to faceplate customized contoured end.

10 Claims, 4 Drawing Sheets

(52) U.S. Cl.
CPC . *A61M 2205/0216* (2013.01); *A61M 2207/00* (2013.01); *Y10T 29/49828* (2015.01)

(58) Field of Classification Search
CPC ...... A61M 16/0622; A61M 2205/0216; A61M 2207/00
See application file for complete search history.

(56) References Cited

U.S. PATENT DOCUMENTS

| | | | |
|---|---|---|---|
| 6,412,487 B1 | 7/2002 | Gunaratnam | |
| 8,826,908 B2 | 9/2014 | Drew | |
| 8,869,798 B2 | 10/2014 | Wells | |
| 2005/0199239 A1 | 9/2005 | Lang | |
| 2006/0042629 A1 | 3/2006 | Geist | |
| 2006/0124131 A1* | 6/2006 | Chandran | A61M 16/06 128/206.28 |
| 2008/0047560 A1* | 2/2008 | Veliss | A61M 16/06 128/206.24 |
| 2008/0230067 A1* | 9/2008 | Kwok | A61M 16/0666 128/206.24 |
| 2009/0267261 A1 | 10/2009 | Mark | |
| 2010/0095556 A1* | 4/2010 | Jarvis | A43B 1/0027 36/107 |
| 2010/0108072 A1 | 5/2010 | D'Souza | |
| 2010/0319700 A1* | 12/2010 | Ng | A61M 16/06 128/206.28 |
| 2013/0239972 A1* | 9/2013 | McAuley | A61M 16/0683 128/205.25 |
| 2014/0352134 A1* | 12/2014 | Ho | A61M 16/06 29/592 |
| 2015/0265794 A1* | 9/2015 | De Kruyff | A61M 16/06 128/200.23 |

FOREIGN PATENT DOCUMENTS

| | | |
|---|---|---|
| EP | 1116492 A2 | 7/2001 |
| FR | 2824739 A1 | 11/2002 |
| JP | 2010207622 A | 9/2010 |
| JP | 2011229997 A | 11/2011 |
| JP | 2012501763 A | 1/2012 |
| WO | WO0059567 A1 | 10/2000 |
| WO | WO2011049548 A1 | 4/2011 |

\* cited by examiner

RESPIRATORY INTERFACE DEVICE CUSTOMIZATION UTILIZING A GENERIC CUSHION TEMPLATE

CROSS-REFERENCE TO RELATED APPLICATIONS

This patent application claims the priority benefit under 35 U.S.C. § 371 of international patent application no. PCT/IB2013/060658, filed Dec. 5, 2013, which claims the priority benefit under 35 U.S.C. § 119(e) of U.S. Provisional Application No. 61/737,316, filed on Dec. 14, 2012, the contents of which are herein incorporated by reference.

BACKGROUND OF THE INVENTION

1. Field of the Invention

The present invention relates to respiratory interface devices for transporting a gas to and/or from an airway of a user and in particular to a faceplate including a customized contoured end to which a cushion may be coupled.

2. Description of the Related Art

A variety of respiratory interface devices are known in the art. These interface devices include a mask, or respiratory interface device, through which gases can be provided (e.g., at a positive pressure) for consumption by the user. Such masks include, without limitation, nasal/oral masks that fit over the mouth and nose of the user, nasal masks which fit over only the nose of the user, and nasal pillows with prongs which fit into the nares of the user. It is known to maintain such interfaces on the face of a user by a headgear that wraps around the head of the user. The uses for such interface devices include high altitude breathing (aviation applications), swimming, mining, fire fighting and various medical diagnostic and therapeutic applications.

One requisite of many of these interface devices, particularly medical respiratory interface devices, is that they provide an effective fit against the user's face to limit or prevent leakage of the gas being supplied. In an exemplary embodiment, masks include a rigid faceplate and a resilient, flexible cushion. The cushion is coupled to the faceplate. Thus, the rigid faceplate provides support and maintains the general shape of the cushion. The cushion is structured to contact the user's face.

With the exception of custom made interface devices, faceplates and cushions are mass produced and are therefore generic. That is, the faceplates and cushions are not generally customized for a specific user. Masks including such faceplates and cushions provide a generally continuous seal against the user's face. A customized mask, however, provides a more complete seal.

A customized mask is based on a user's facial contours. That is, a user has their face scanned, or otherwise modeled, to create a user's 3D surface profile. The user's 3D surface profile is used to design a custom mask structured to substantially match the contours of the user's face. The custom mask is then produced for that user. Such a custom mask is structured to better engage the contours of the user's face. A custom mask may include a unitary faceplate and cushion. That is, the faceplate and cushion are molded as a single piece. Such custom masks are expensive. Moreover, the cushion is subject to wear and tear. Thus, when the cushion deteriorates, a new custom mask must be created.

Some custom masks utilize a custom cushion. That is, the faceplate is generic, but a custom cushion is created for a user based on a user's 3D surface profile, e.g. a facial profile. A user may have multiple cushions created, thereby reducing cost, but custom cushions are still expensive. Further, the user's supply of custom cushions will eventually need to be replenished. This means that either the manufacturer will need to maintain the molds for each user, or, the user will need to have a new mold made each time their supply of cushions needs to be replenished.

Accordingly a need exists for a mask that provides the advantages of a custom respiratory interface device, but that is less expensive to produce or which utilizes generic cushions while still providing a custom configuration.

SUMMARY OF THE INVENTION

One embodiment of the present invention provides a respiratory interface device including a cushion structured to be coupled to a faceplate, a faceplate including a peripheral end, and a coupling assembly. The faceplate peripheral end includes a formable material and wherein a portion of the faceplate peripheral end is a customized contoured end. The cushion is coupled to the faceplate adjacent the faceplate customized contoured end. The cushion conforms to the faceplate customized contoured end.

A "formable material," as used herein, is either a removable material 21 or an addable material. A removable material is structured to have portions easily removed without distorting or damaging the remaining portions of faceplate peripheral end. Thus, the remaining portions of the removable material are configured in a selected shape. Addable material is a material that may be selectively added to selected locations of faceplate peripheral end whereby addable material builds up in a selected shape. Addable material may be added by a 3D printing process or a similar process.

Another embodiment provides a respiratory interface device including a cushion structured to be coupled to a faceplate, a faceplate including a customized contoured end, a coupling assembly. The cushion engages the faceplate adjacent the faceplate customized contoured end. The cushion conforms to the faceplate customized contoured end.

It is a further object of this invention to provide a method of making a respiratory interface device including a faceplate with a faceplate customized contoured end including the steps of: acquiring a 3D surface profile of a user's face, determining a faceplate profile for the user's face, providing a generic faceplate including a peripheral end, the faceplate peripheral end including a formable material, adding or removing portions of the faceplate peripheral end formable material until the faceplate substantially matches the faceplate profile for the user's face thereby creating a faceplate customized contoured end, and coupling a cushion to the faceplate customized contoured end.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
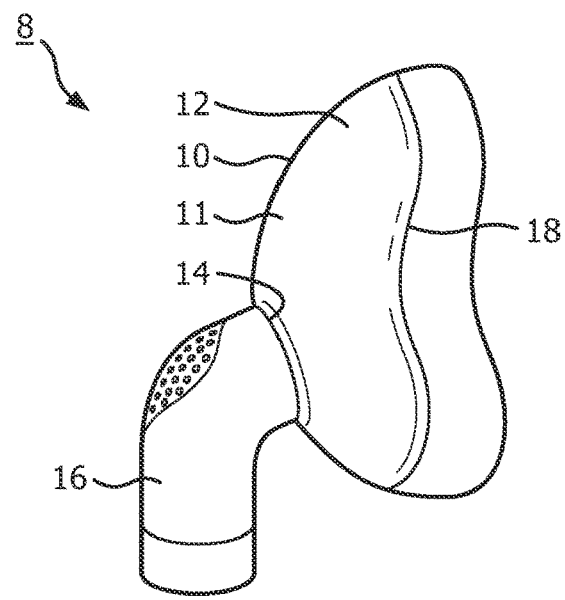
FIG. 1 is an isometric view of a respiratory interface device according to the principles of the present invention.

As used herein, the singular form of "a," "an," and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the statement that two or more parts or components "engage" one another shall means that the parts exert a force against one another either directly or through one or more intermediate parts or components. As used herein, the word "unitary" means a component is created as a single piece or unit. That is, a component that includes pieces that are created separately and then coupled together as a unit is not a "unitary" component or body. As used herein, the term "number" shall mean one or an integer greater than one (i.e., a plurality).

As used herein, a "coupling" is one element of a coupling assembly. That is, a coupling assembly includes at least two components, or coupling components, that are structured to be coupled together. It is understood that the elements of a coupling assembly are compatible with each other. For example, in a coupling assembly, if one coupling element is a snap socket, the other coupling element is a snap plug. As used herein, "generic" means as mass produced, i.e. as multiple components, units, devices, etc. that are substantially similar.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together. In that situation, the difference between the size of the components is even smaller whereby the amount of friction increases. If the element defining the opening and/or the component inserted into the opening are made from a deformable or compressible material, the opening may even be slightly smaller than the component being inserted into the opening.

As used herein, "conform" means that a resilient element, such as but not limited to a cushion, is deformed to correspond to the shape of another element. For example, a custom faceplate may be coupled to a custom cushion with a corresponding shape. In this configuration, the custom cushion does not "conform" to the custom faceplate as the custom cushion has a corresponding shape. Conversely, a generic cushion coupled to a custom faceplate will "conform" to the custom faceplate. That is, the shape of the generic cushion changes/deforms so as to correspond to the shape of the custom faceplate.

As used herein, "a generally continuous seal" may have a gap or may gap when the user moves. As used herein, "a more complete seal" has a gap that is shorter in length than a gap of a generally continuous seal, or, is resistant to gapping when the user moves.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 shows a respiratory interface assembly 8 according to an embodiment of the invention. Respiratory interface assembly 8 includes a respiratory interface device 10 and a support assembly such as, but not limited to straps (not shown). Respiratory interface device 10 is shown as a nasal/oral respiratory interface device 10. It is understood, however, that respiratory interface device 10 can include, without limitation, a nasal mask, nasal pillows, or any other device that provides a suitable gas flow communicating function. Thus, as used herein, the term "respiratory interface device" shall refer to any of such devices. Respiratory interface device 10 is coupled to a pressure generating system (not shown) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV®) device, proportional positive airway pressure (PPAP) device, C-Flex™ device, Bi-Flex® device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device.

Respiratory interface device 10 includes a body 11 with a faceplate 12, a cushion 30, and a coupling assembly 50, as discussed below. In an exemplary embodiment, faceplate 12 is a substantially rigid body. In an exemplary embodiment, shown in FIG. 1, faceplate 12 is a single piece structured to cover the user's nose and mouth. That is, respiratory interface device 10 has a peripheral contour that is structured to extend over a user's nose and mouth. In this embodiment, body 11 is coextensive with faceplate 12. Faceplate 12 defines lower opening 14. Lower opening 14 can function as a gas inlet. Gas inlet (lower opening 14) can be coupled to a coupling device 16, such as a swivel conduit, for carrying gas such as air between respiratory interface device 10 and an external gas source (not shown), such as a blower, or any other suitable device. It is contemplated that the external gas source can encompass, without limitation, any gas delivery or gas generation system capable of supplying gas for consumption by a user.

Non-limiting examples of various gas delivery therapies can include but are not limited to continuous positive airway pressure (CPAP) therapy, auto-titration positive airway pressure therapy, and bi-level positive airway pressure (BiPAP) therapy, as noted above. The particular coupling device 16, shown in FIG. 1, is not meant to be limiting and it should be understood that the present invention contemplates a variety of different coupling devices that could be attached, either permanently or selectively, to lower opening 14 to carry gas to or from respiratory interface device 10. Thus, a variety of coupling devices (e.g., with or without swivels on one or both ends, and with or without an exhalation system formed integral to the device) may be substituted for coupling device 16.

Figure 2:
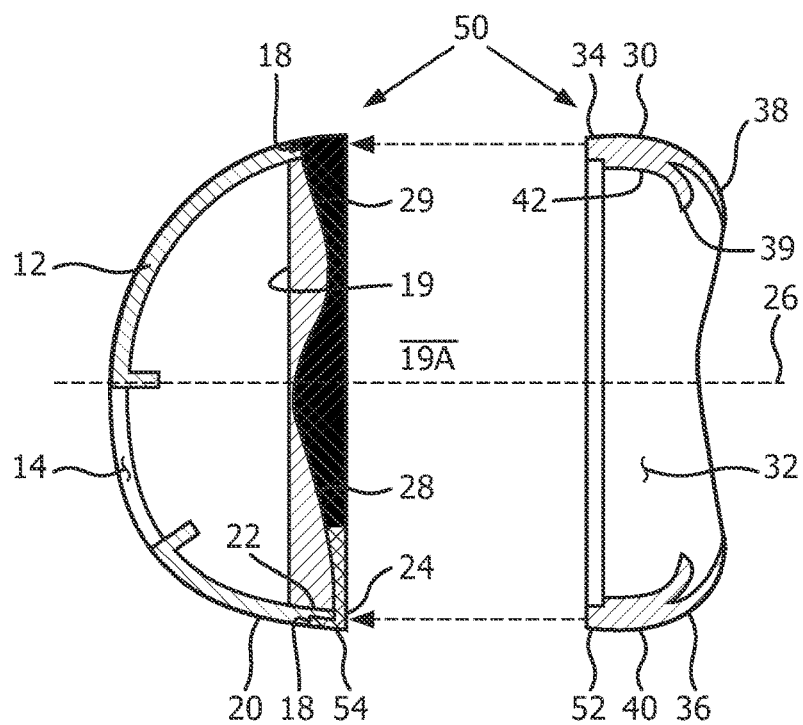
FIG. 2 is a cross-sectional exploded view of portions of the respiratory interface device of FIG. 1.

In an exemplary embodiment, shown in FIG. 2, faceplate 12 is generally convex or bowl-shaped. This shape defines an interior space that accommodates a user's nose and other features when respiratory interface device 10 is in use. Faceplate 12 includes a peripheral end 18 that extends about faceplate 12. In this exemplary embodiment, faceplate peripheral end 18 extends generally towards the user's face when respiratory interface device 10 is in use. Faceplate peripheral end 18 includes an outer side 20, an inner side 22, and an axial side 24. Further, faceplate 12 has an axis 26 extending generally perpendicular to the plane of peripheral end 18. As used herein, the terms "axial" and "radial" are used in relation to axis 26.

Faceplate 12 is made from a rigid or semi-rigid polymer such as, but not limited to, polycarbonate, nylon, polyethylene, polypropylene, or even a harder silicone (having a hardness of about 60 shore A). A portion, as defined below, of faceplate peripheral end 18 is made from polycarbonate, nylon, polyethylene poly propylene, aluminum, composite material (e.g. 3D printing material). The material that comprises faceplate peripheral end 18 is a formable material 19.

A "formable material" 19, as used herein, is either a removable material 21 or an addable material 23. Removable material 21 is structured to have portions easily removed without distorting or damaging the remaining portions of faceplate peripheral end 18. Thus, the remaining portions of removable material 21 are configured in a selected shape. Addable material 23 is a material that may be selectively added to selected locations of faceplate peripheral end 18 whereby addable material 23 builds up in a selected shape. Addable material 23 may be added by a 3D printing process or a similar process.

As shown in an exemplary embodiment, formable material 19 is a removable material 21. That is, in this embodiment, the material that comprises faceplate peripheral end 18 is structured to have portions easily removed without distorting or damaging the remaining portions of faceplate peripheral end 18. Removable material 21 is shown with single hatching and an exemplary removed area 21A is shown in cross-hatching. Removable material 21 may be a thermoplastic. such as, but not limited to, polycarbonate, acetal, nylon, or ultem.

Faceplate 12, and more specifically faceplate peripheral end 18, is initially made with a generic shape. In the exemplary embodiment, as shown in FIG. 2, faceplate peripheral end 18 with a generic shape is shown as generally planar. It is understood that faceplate peripheral end 18 with a generic shape may be any shape. Faceplate peripheral end 18 is structured to have portions removed therefrom, or, added thereto. When faceplate peripheral end 18 has portions removed therefrom, or, added thereto, as described below, faceplate peripheral end 18 becomes a customized contoured end 28. A "portion" of faceplate peripheral end 18 means any portion that is larger than nothing. Thus, faceplate customized contoured end 28 may be a small portion of faceplate peripheral end 18 or the entire faceplate peripheral end 18. A "customized contoured end," as used herein, is faceplate peripheral end 18 that has been shaped for a specific user.

As described below, a generic cushion 30 conforms to faceplate customized contoured end 28. Thus, respiratory interface device 10, including faceplate customized contoured end 28, acts as customized respiratory interface device 10 rather than as generic respiratory interface device 10. That is, a generic respiratory interface device 10 provides a generally continuous seal against the user's face when in use. A customized respiratory interface device 10 provides a more complete seal against the user's face when in use.

Removable material 21 of faceplate peripheral end 18 that is removed may be removed by cutting with a blade, laser cutting, water jet cutting, grinding, sanding or any similar method. In an exemplary embodiment, faceplate peripheral end 18 is milled (rotary grinding) to remove a portion of the material. Thus, in an exemplary embodiment, faceplate customized contoured end 28 includes a milled surface 29.

Figure 9:
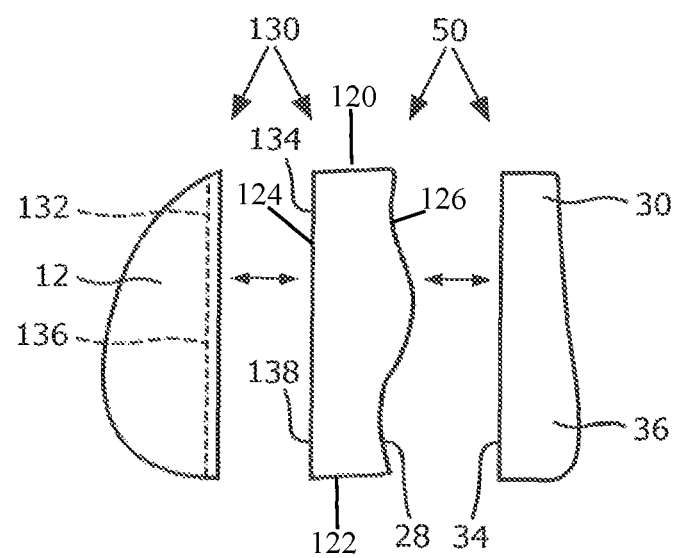
FIG. 9 is an exploded view of a respiratory interface device according to a further embodiment of the invention.

In an alternate embodiment, formable material 19 is an addable material 21. In an exemplary embodiment, addable material 21 is applied in layers wherein addable material 21 is applied in greater or lesser quantities as needed to form the desired shape. Addable material 21 may be applied as a liquid that dries to a rigid material. Addable material 21 may be applied directly to a generic faceplate 12. That is, as shown in FIG. 9, generic faceplate 12 includes a generally planar peripheral end 18. Addable material 21 is applied to faceplate peripheral end 18 thereby changing the shape of faceplate peripheral end 18 so as to create faceplate customized contoured end 28. In an exemplary embodiment, addable material 21 may be applied as a thin walled, shaped member 120. It is understood, however, that addable material 21 may be applied may be applied in any shape that creates faceplate customized contoured end 28.

In another embodiment, shaped member 120 is created separately from faceplate 12 and is then coupled to faceplate 12. In this embodiment, shaped member 120 and shaped member coupling device 130 (discussed below) are part of the faceplate 12. As shown in FIG. 9, shaped member 120 is a body 122 including a proximal end 124 and a distal end 126. A shaped member coupling device 130 is structured to couple, directly couple, or fix shaped member 120 to faceplate 12. That is, shaped member coupling device 130 includes a faceplate component 132 and a shaped member component 134, discussed below. Shaped member body distal end 126 is shaped to create faceplate customized contoured end 28. Further, shaped member body distal end 126 includes coupling assembly 50, discussed below.

Shaped member coupling device faceplate component 132 is disposed on faceplate 12. Shaped member body proximal end 124 includes shaped member coupling device shaped member component 134. For example, as shown, shaped member coupling device faceplate component 132 is a faceplate groove 136 in faceplate peripheral end 18. Shaped member body proximal end 124 is sized to snuggly correspond to faceplate groove 136. As such, shaped member body proximal end 124 acts as a tongue 138 that is held in faceplate groove 136 in a press-fit manner. Other shaped member coupling devices 130 may be used as well. For example, shaped member coupling device 130 may include pins structured to snuggly fit into corresponding bores, a resilient latch structured to engage a slot, or two opposing latch surfaces that engage each other (none shown). The components of shaped member coupling device 130 may further be secured to faceplate 12 by an adhesive or sonic welding.

Cushion 30 is structured to extend from faceplate 12 toward the user's face and generally defines the depth of respiratory interface device 10. Cushion 30 is, in an exemplary embodiment, a body made from a resilient, flexible, i.e. low durometer, material such as, but not limited to, silicone or polyurethane that has a hardness between about 25 shore OO and 40 shore A. Cushion 30 defines a primary passage 32. That is, cushion 30 is hollow and, essentially, a shallow tube. It is understood that respiratory interface device 10, and therefore cushion 30, may have any shape. Cushion 30 has an inner end 34, a sidewall 36, and an outer end 38. Cushion 30 further has an outer side 40 and an inner side 42. Cushion outer end 38 is structured to contact a user's face and may be curled toward axis 26 and may include one or more additional flaps 39. Cushion inner end 34 is structured to engage faceplate customized contoured end 28. When cushion inner end 34 engages faceplate customized contoured end 28, cushion 30 conforms to the shape of customized contoured end 28. That is, the flexible body of cushion 30 adapts its shape in response to the shape of faceplate customized contoured end 28.

As described below, cushion 30 is coupled to faceplate 12 and, more specifically, directly coupled to faceplate customized contoured end 28. While faceplate 12 becomes customized, i.e. faceplate 12 is no longer generic, following the forming of the faceplate customized contoured end 28, i.e. removal of a portion of faceplate peripheral end 18 or adding material to faceplate peripheral end 18, cushion 30 is, in an exemplary embodiment, always generic. That is, while cushion 30 adapts its shape in response to the shape of faceplate customized contoured end 28 and therefore be configured in a non-generic shape, cushion 30 is a generic cushion and, absent engagement with faceplate customized contoured end 28, has a generic shape.

As noted above, respiratory interface device 10 includes coupling assembly 50. Coupling assembly 50 is structured to couple faceplate 12 and cushion 30. Coupling assembly 50 includes a first component 52 and a second component 54. It is understood that one coupling component is disposed on, and may be unitary with, each of faceplate 12 and cushion 30. As discussed in the exemplary embodiment below, coupling assembly first component 52 will be associated with cushion 30 and will be identified as "cushion first coupling component 52." Similarly, coupling assembly second component 54 will be associated with faceplate 12 and will be identified as "faceplate second coupling component 54." Further, it is noted that specific embodiments of coupling assembly 50 may include a number of similar coupling components 52, 54 disposed at discrete locations about faceplate peripheral end 18 and cushion inner end 34, or, the coupling components 52, 54 may extend about, or substantially about, faceplate peripheral end 18 and cushion inner end 34.

Cushion inner end 34 includes cushion first coupling component 52. Faceplate 12 includes faceplate second coupling component 54 and, in an exemplary embodiment, faceplate second coupling component 54 is disposed adjacent faceplate peripheral end 18. Cushion first coupling component 52 and faceplate second coupling component 54 are structured to be coupled together. Coupling assembly 50, and therefore cushion first coupling component 52 and faceplate second coupling component 54, are selected from the group, shown in FIGS. 3-7, including: a tongue-and-groove coupling assembly 50A, a strap-and-peg coupling assembly 50B, a resilient snap coupling assembly 50C, a press-fit coupling assembly 50D, and a sheath coupling assembly 50E. These coupling assemblies, collectively hereinafter "coupling assembly 50," are discussed below. In FIGS. 3-7, each coupling assembly 50 is shown in a separated configuration.

Figure 3:
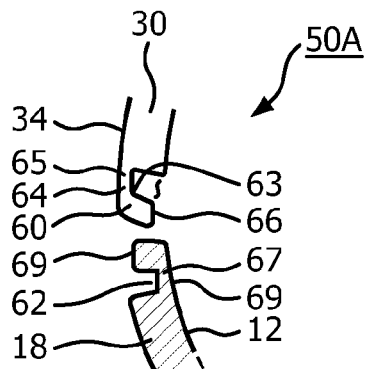
FIG. 3 is a cross-sectional view of one embodiment of a coupling assembly according to the principles of the present invention.

In an exemplary embodiment, shown in FIG. 3, tongue-and-groove coupling assembly 50A, cushion first coupling component 52 is a radially extending tongue 60 and faceplate second coupling component 54 is a radially recessed groove 62. Cushion first coupling component tongue 60 is a planar extension from cushion 30. Faceplate second coupling component groove 62 is disposed adjacent faceplate peripheral end 18. Cushion first coupling component tongue 60 and faceplate coupling component groove 62 have a corresponding cross-sectional shape and cushion first coupling component tongue 60 fits snuggly within faceplate second coupling component groove 62.

In an exemplary embodiment, cushion first coupling component tongue 60 extends inwardly, i.e. from cushion inner side 40 at, or adjacent, cushion inner end 34. Accordingly, faceplate second coupling component groove 62 is an outwardly facing groove 62 disposed adjacent faceplate peripheral end 18. In an exemplary embodiment, cushion first coupling component tongue 60 and faceplate second coupling component groove 62 extend about respiratory interface device body 11. That is, cushion first coupling component tongue 60 extends about cushion inner end 34 and faceplate second coupling component groove 62 extends about faceplate peripheral end 18.

In another exemplary embodiment, cushion first coupling component 52 is a radially extending tongue 60 wherein cushion first coupling component tongue 60 is a radially extending portion of an L-shaped extension 64. That is, cushion first coupling component L-shaped extension 64 is disposed at cushion inner end 34. The cushion first coupling component L-shaped extension 64 includes an axially extending portion 65 and a radially extending portion 66. Similarly, faceplate second coupling component 54 is an L-shaped extension 67. Faceplate second coupling component L-shaped extension 67 also includes an axially extending portion 68 and a radially extending portion 69. Faceplate second coupling component groove 62 is formed by faceplate peripheral end axial side 24 and faceplate second coupling component L-shaped extension 67.

It is noted that cushion first coupling component L-shaped extension 64 and cushion inner end 34 also forms a groove 63. In an exemplary embodiment, cushion first coupling component L-shaped extension 64 and faceplate second coupling component L-shaped extension 67 are similarly sized. In this configuration, faceplate second coupling component L-shaped extension axially extending portion 68 may be disposed in groove 63, and, cushion first coupling component L-shaped extension radially extending portion 64, which is cushion first coupling component tongue 60, is disposed in faceplate second coupling component groove 62.

Figure 4:
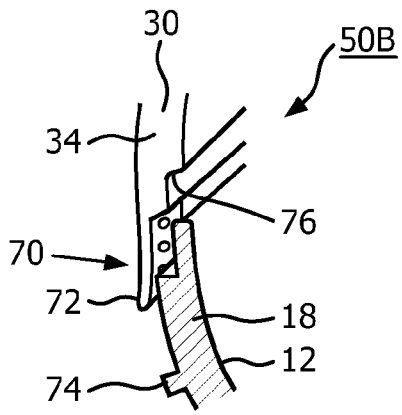
FIG. 4 is a cross-sectional view of another embodiment of a coupling assembly according to the principles of the present invention.

In another exemplary embodiment, shown in FIG. 4, strap-and-peg coupling assembly 50B includes a number of similar coupling components 52, 54 disposed at discrete locations about faceplate peripheral end 18 and cushion inner end 34. Thus it is understood that cushion first coupling component 52 is a number of sets of openings 70

(discussed below) and that faceplate second coupling component 54 is a number of radially extending lugs 74 (discussed below), but only one such pair of coupling components 52, 54 will be specifically discussed. It is understood that there are a number of such pairs of coupling components 52, 54 disposed about faceplate peripheral end 18 and cushion inner end 34. It is noted that cushion first coupling component number of sets of openings 70 and faceplate second coupling component number of radially extending lugs 74 are positioned to substantially correspond to, i.e. be aligned with, each other.

In this embodiment, cushion first coupling component 52 is a set of openings 70 disposed about the cushion inner end 34. As shown, cushion inner end 34 includes a number of generally axially extending straps 72. Cushion first coupling component set of openings 70 are disposed on strap 72. Cushion first coupling component set of openings 70 are disposed in a generally axial line. Faceplate second coupling component 54 is a radially extending lug 74. Strap 72 is, in an exemplary embodiment, unitary with cushion 30 and is, therefore, resilient. Thus, strap 72 may be stretched, if necessary, to position an opening in cushion first coupling component set of openings 70 over faceplate second coupling component lug 74. Faceplate second coupling component lug 74 is then passed through an opening in cushion first coupling component set of openings 70.

Strap-and-peg coupling assembly 50B further includes a mounting surface 76. Mounting surface 76 extends generally radially. Mounting surface 76 is structured to be coupled to, and in one exemplary embodiment directly coupled to, faceplate customized contoured end 28.

Figure 5:
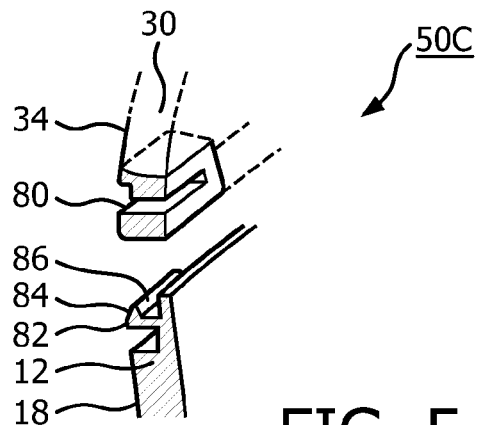
FIG. 5 is a cross-sectional view of another embodiment of a coupling assembly according to the principles of the present invention.

In another exemplary embodiment, shown in FIG. 5, resilient snap coupling assembly 50C includes a number of similar coupling components 52, 54 disposed at discrete locations about faceplate peripheral end 18 and cushion inner end 34. Thus, it is understood that cushion first coupling component 52 is a number of radial openings 80 (discussed below) and that faceplate second coupling component 54 is a number of radially extending latch members 82 (discussed below), but only one such pair of coupling components 52, 54 will be specifically discussed. It is understood that there are a number of such pairs of coupling components 52, 54 disposed about faceplate peripheral end 18 and cushion inner end 34. It is noted that cushion first coupling component number of radial openings 80 and faceplate second coupling component radially extending latch members 82 are positioned to substantially correspond to, i.e. be aligned with, each other.

In this embodiment, cushion first coupling component 52 is radial opening 80 and faceplate second coupling component 54 is radially extending latch member 82. Faceplate second coupling component radially extending latch member 82 includes an angled outer side 84 and a generally axially extending latch side 86. Faceplate second coupling component radially extending latch member 82 is passed through cushion first coupling component radial opening 80 and latched in place by axially extending latch side 86.

Figure 6:
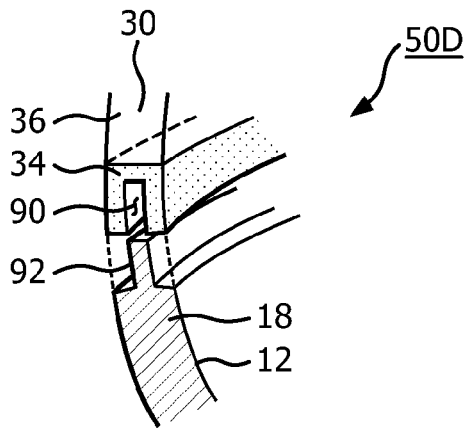
FIG. 6 is a cross-sectional view of another embodiment of a coupling assembly according to the principles of the present invention.

In another exemplary embodiment, shown in FIG. 6, press-fit coupling assembly 50D includes cushion first coupling component 52 that is an axial channel 90 and faceplate second coupling component 54 that is a ridge 92 extending axially from faceplate peripheral end 18. Cushion first coupling component axial channel 90 is a channel that faces generally axially. That is, cushion first coupling component axial channel 90 is a channel in the axial face of cushion inner end 34. Faceplate second coupling component ridge 92 is a planar ridge that extends axially from faceplate peripheral end 18, including the portions that are faceplate customized contoured end 28. Cushion first coupling component axial channel 90 and faceplate second coupling component ridge 92 have a corresponding cross-sectional shape and faceplate second coupling component ridge 92 fits snuggly within cushion first coupling component axial channel 90. In an exemplary embodiment, cushion first coupling component axial channel 90 and faceplate second coupling component ridge 92 extend about respiratory interface device body 11. That is, cushion first coupling component axial channel 90 extends about cushion inner end 34 and faceplate second coupling component ridge 92 extends about faceplate peripheral end 18.

It is understood that the positions of the cushion first coupling component 52 and the faceplate second coupling component 54 of this embodiment may be reversed. That is, the cushion first coupling component 52 may be a ridge (not shown) and faceplate second coupling component 54 may be a channel (not shown). Further, in either configuration, the channel, e.g. cushion first coupling component axial channel 90 may include inwardly extending barbs or teeth (not shown) to help secure the other coupling component 52, 54 in the channel. Further, and in another exemplary embodiment, an adhesive (not shown) may be disposed in cushion first coupling component axial channel 90 to assist in securing the first and second coupling components 52, 54 together.

In another exemplary embodiment, cushion inner end 34 is made from a material that is stiffer than other portions of cushion 30. That is, cushion sidewall 36 and outer end 38 are made from a material with a first hardness. Cushion inner end 34 is made from a material with a second hardness. The material with a second hardness is harder than the material with a first hardness. More specifically, the material with a second hardness has a hardness between about 20 and 100 shore A.

Figure 7:
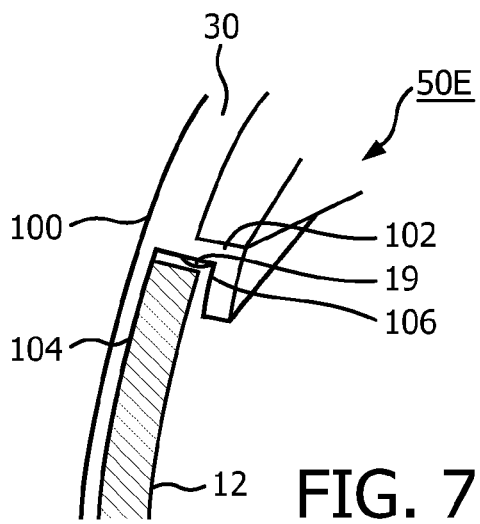
FIG. 7 is a cross-sectional view of another embodiment of a coupling assembly according to the principles of the present invention.

In another exemplary embodiment, shown in FIG. 7, a sheath coupling assembly 50E includes a cushion first coupling component 52 that is a resilient sheath 100 and a radially, inwardly extending rib 102, and, faceplate second coupling component 54 that includes a mounting surface 104 and a latching surface 106. Faceplate second coupling component mounting surface 104 is a portion of the outer surface of faceplate 12. In an exemplary embodiment, faceplate second coupling component mounting surface 104 is a peripheral portion of the outer surface of faceplate 12. Faceplate second coupling component latching surface 106 is a radial surface on, or adjacent, faceplate peripheral end 18. Faceplate second coupling component latching surface 106 may be the axial side of faceplate peripheral end 18 and includes faceplate customized contoured end 28. Cushion first coupling component sheath 100 extends axially from cushion inner end 34 and is made from a resilient material. Cushion first coupling component sheath 100 may be shaped to correspond to the shape of the outer surface of faceplate 12. Thus, cushion first coupling component sheath 100 is structured to be coupled to faceplate second coupling component mounting surface 104.

Cushion first coupling component sheath 100 includes an opening, not shown, structured to extend about coupling device 16. Cushion first coupling component inwardly extending rib 102 is disposed at the interface of cushion first coupling component resilient sheath 100 and cushion inner end 34. Cushion first coupling component inwardly extending rib 102 is structured to be coupled to faceplate second coupling component latching surface 106 which is faceplate peripheral end 18 and includes faceplate customized contoured end 28.

To utilize sheath coupling assembly 50E, faceplate 12 is passed through cushion 30 and, more specifically, passed through cushion 30 starting at cushion second end 38 toward cushion first end 34. Faceplate 12 is oriented so that faceplate second coupling component mounting surface 104, i.e. the outer side of faceplate 12, faces cushion 30 prior to being passed therethrough. As faceplate 12 passes through cushion 30, faceplate second coupling component mounting surface 104 contacts cushion first coupling component resilient sheath 100. Faceplate 12 is moved into cushion first coupling component resilient sheath 100 until cushion first coupling component inwardly extending rib 102 directly contacts faceplate second coupling component latching surface 106. It is understood that cushion first coupling component sheath opening is positioned about coupling device 16.

It is noted that in all embodiments disclosed above, coupling assembly 50 is disposed adjacent faceplate customized contoured end 28. As such, cushion 30 is coupled to faceplate 12 adjacent faceplate customized contoured end 28. In this configuration, cushion 30 conforms to faceplate customized contoured end 28. That is, the shape of resilient, flexible cushion 30 changes as a result of the contour of faceplate customized contoured end 28. In an exemplary embodiment, that shape of cushion 30 changes to be similar to the contour of faceplate customized contoured end 28. Thus, in this configuration a generic cushion 30 acts as a customized cushion 30 when coupled to faceplate 12 having faceplate customized contoured end 28. It is further noted that the resilient nature of cushion 30 causes cushion 30 to apply a force to faceplate 12. That is, cushion 30 is generic cushion 30 that is not shaped to correspond to faceplate customized contoured end 28. Thus, when cushion 30 conforms to faceplate customized contoured end 28, the resilient nature of the material forming cushion 30 creates a force that acts on faceplate 12.

Accordingly, a user may have their facial contours measured and recorded as a user's 3D surface profile. The measuring and recording of the user's facial contours may be performed by a 3D scanning device or any other known method. It is understood that such a user's 3D surface profile may be limited to selected portions of the face. Based on this data, a faceplate profile for a user may be determined. That is, the "faceplate profile" is the shape for faceplate 12, and more specifically faceplate 12 that has customized contoured end 28, should have to provide a more complete seal between cushion 30 and the user's face. A customized faceplate 12 is then created by forming selected portions of formable material 19 of faceplate peripheral end 18. As noted above, this process creates a faceplate customized contoured end 28. Cushion 30 is then coupled to faceplate 12. When cushion 30 is coupled to faceplate 12, cushion 30 engages faceplate customized contoured end 28. As noted above, cushion 30, which is a generic cushion, conforms to faceplate customized contoured end 28. In this configuration, cushion 30 provides a more complete seal than a generic cushion coupled to a generic faceplate.

Figure 8:
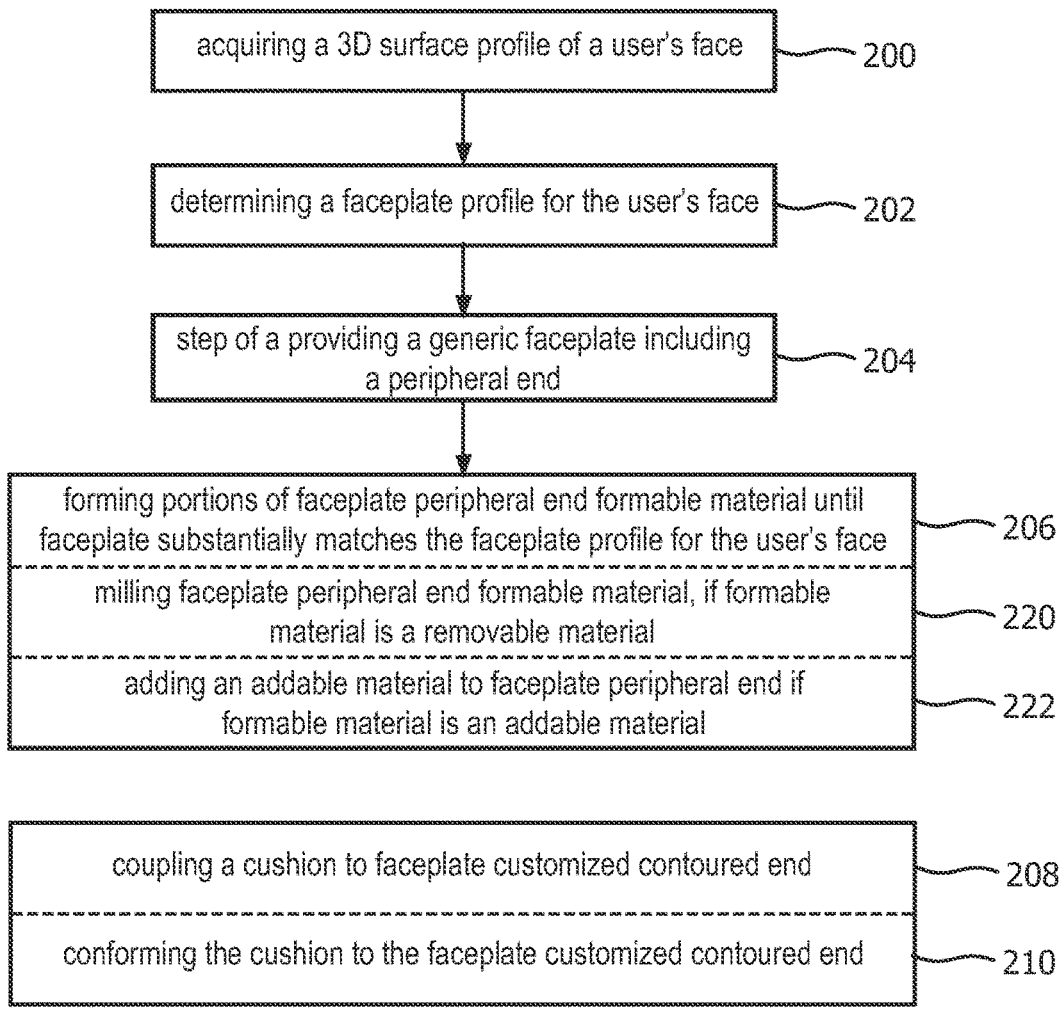
FIG. 8 is a flow chart if the steps of the disclosed method according to the principles of the present invention.

Accordingly, as shown in FIG. 8, a method of making respiratory interface device 8 including faceplate 12 with faceplate customized contoured end 28 includes the steps of acquiring 200 a 3D surface profile of a user's face, determining 202 a faceplate profile for the user's face, providing 204 a generic faceplate including a peripheral end, faceplate peripheral end including a formable material, forming 206 portions of faceplate peripheral end formable material until faceplate substantially matches the faceplate profile for the user's face thereby creating a faceplate customized contoured end, and, coupling 208 cushion to faceplate customized contoured end. That is, acquiring 200 a 3D surface profile of a user's face may be accomplished by any method for capturing 3D data. Further, determining 202 a faceplate profile for the user's face means determining the shape of faceplate 12 that will provide a more complete seal between cushion 30 and the user's face. The faceplate profile is, in an exemplary embodiment, stored in an electronic format as a 3D model.

Forming 206 portions of faceplate peripheral end formable material until faceplate substantially matches the faceplate profile for the user's face means that portions of faceplate peripheral end formable material are formed until the shape of faceplate 12 substantially matches the shape of the faceplate profile. Thus, the step of forming 206 portions of faceplate peripheral end formable material until faceplate substantially matches the faceplate profile for the user's face thereby creating a faceplate customized contoured end 28 may include either, or both, the steps of milling 220 faceplate peripheral end formable material 19, if formable material 19 is a removable material 21, and/or, adding 222 an addable material 23 to faceplate peripheral end 18 if formable material 19 is an addable material 23. In an exemplary embodiment, only faceplate peripheral end 18 has to substantially match the shape of faceplate peripheral end in the faceplate profile. That is, the generic portions of faceplate 12 may be ignored.

The step of coupling 208 a cushion to faceplate customized contoured end includes the step of conforming 210 the cushion to the faceplate customized contoured end. Further, the step of coupling 208 cushion to faceplate customized contoured end utilizes a coupling assembly selected from the group including: a tongue-and-groove coupling assembly 50A, a strap-and-peg coupling assembly 50B, a resilient snap coupling assembly 50C, a press-fit coupling assembly 50D, and a sheath coupling assembly.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory interface device comprising:
   a faceplate having a peripheral end, wherein the peripheral end includes a formable material, and wherein a portion of the peripheral end is a customized contoured end;
   a generic cushion structured to be coupled to the faceplate;
   a coupling assembly adapted to couple the generic cushion to the faceplate such that the generic cushion conforms to the faceplate customized contoured end;
   wherein the formable material is a removable material;
   the peripheral end includes an axial side; and
   wherein the peripheral end axial side includes a milled surface.

2. A respiratory interface device comprising:
   a faceplate having a peripheral end, wherein the peripheral end includes a formable material, and wherein a portion of the peripheral end is a customized contoured end;
   a generic cushion structured to be coupled to the faceplate;
   a coupling assembly adapted to couple the generic cushion to the faceplate such that the generic cushion conforms to the faceplate customized contoured end; and
   wherein the formable material is an addable material.

3. The respiratory interface device of claim 2, wherein the formable material includes a shaped member and a shaped member coupling device, and wherein the shaped member coupling device is structured to couple the shaped member to the faceplate.

4. The respiratory interface device of claim 3, wherein the shaped member coupling device includes a faceplate component and a shaped member component, the shaped member including a body including a proximal end and a distal end; the shaped member coupling device shaped member component disposed at the shaped member body proximal end; and the shaped member coupling device faceplate component disposed on the faceplate.

5. A respiratory interface device comprising:
   a faceplate having a peripheral end, wherein the peripheral end includes a formable material, and wherein a portion of the peripheral end is a customized contoured end;
   a generic cushion structured to be coupled to the faceplate;
   a coupling assembly adapted to couple the generic cushion to the faceplate such that the generic cushion conforms to the faceplate customized contoured end;
   the generic cushion includes an inner end and an outer end;
   the coupling assembly includes a first coupling component and a second coupling component;
   the coupling assembly first coupling component is disposed adjacent the generic cushion inner end;
   the coupling assembly second coupling component is disposed adjacent the faceplate;
   the generic cushion first coupling component and the faceplate second coupling component are structured to be coupled together; and
   wherein the generic cushion first coupling component is a radially extending tongue, and the faceplate second coupling component is a radially recessed groove disposed adjacent to the faceplate peripheral end.

6. The respiratory interface device of claim 5, wherein the generic cushion first coupling component includes an L-shaped extension, and the faceplate second coupling component includes an L-shaped extension.

7. A respiratory interface device comprising:
   a faceplate having a peripheral end, wherein the peripheral end includes a formable material, and wherein a portion of the peripheral end is a customized contoured end;
   a generic cushion structured to be coupled to the faceplate;
   a coupling assembly adapted to couple the generic cushion to the faceplate such that the generic cushion conforms to the faceplate customized contoured end;
   the generic cushion includes an inner end and an outer end;
   the coupling assembly includes a first coupling component and a second coupling component;
   the coupling assembly first coupling component is disposed adjacent the generic cushion inner end;
   the coupling assembly second coupling component is disposed adjacent the faceplate;
   the generic cushion first coupling component and the faceplate second coupling component are structured to be coupled together;
   the generic cushion first coupling component is a number of sets of openings disposed about the generic cushion inner end;
   each set of openings including a number of openings, the openings disposed in a generally axial line;
   the faceplate second coupling component includes a number of radially extending lugs; and
   the generic cushion first coupling component number of sets of openings and the faceplate second coupling component number of radially extending lugs are positioned to substantially correspond to each other.

8. A respiratory interface device comprising:
   a faceplate having a peripheral end, wherein the peripheral end includes a formable material, and wherein a portion of the peripheral end is a customized contoured end;
   a generic cushion structured to be coupled to the faceplate;
   a coupling assembly adapted to couple the generic cushion to the faceplate such that the generic cushion conforms to the faceplate customized contoured end;
   the generic cushion includes an inner end and an outer end;
   the coupling assembly includes a first coupling component and a second coupling component;
   the coupling assembly first coupling component is disposed adjacent the generic cushion inner end;
   the coupling assembly second coupling component is disposed adjacent the faceplate;
   the generic cushion first coupling component and the faceplate second coupling component are structured to be coupled together;
   the generic cushion first coupling component is a number of radial openings disposed about the generic cushion inner end;
   the faceplate second coupling component is a number of radially extending latch members disposed adjacent to the faceplate peripheral end; and
   the generic cushion first coupling component number of radial openings and the faceplate second coupling component number of radially extending latch members positioned to substantially correspond to each other.

9. A respiratory interface device comprising:
a faceplate having a peripheral end, wherein the peripheral end includes a formable material, and wherein a portion of the peripheral end is a customized contoured end;
a generic cushion structured to be coupled to the faceplate;
a coupling assembly adapted to couple the generic cushion to the faceplate such that the generic cushion conforms to the faceplate customized contoured end;
the generic cushion includes an inner end and an outer end;
the coupling assembly includes a first coupling component and a second coupling component;
the coupling assembly first coupling component is disposed adjacent the generic cushion inner end;
the coupling assembly second coupling component is disposed adjacent the faceplate;
the generic cushion first coupling component and the faceplate second coupling component are structured to be coupled together;
wherein the generic cushion first coupling component is an axial channel, and the faceplate second coupling component is a ridge extending axially from the faceplate peripheral end;
the generic cushion includes a sidewall disposed between the generic cushion inner end and the generic cushion outer end;
the generic cushion sidewall is made from a material with a first hardness;
the generic cushion inner end is made from a material with a second hardness;
the material with a second hardness is harder than the material with a first hardness; and
the generic cushion first coupling component is disposed on the generic cushion inner end.

10. A method of making a respiratory interface device including a faceplate with a faceplate customized contoured end comprising the steps of:
acquiring a 3D surface profile of a user's face;
determining a faceplate profile for the user's face;
providing a generic faceplate including a peripheral end;
including a formable material at the generic faceplate peripheral end;
forming portions of the faceplate peripheral end formable material until the faceplate substantially matches the faceplate profile for the user's face thereby creating the faceplate customized contoured end;
coupling a generic cushion to the faceplate customized contoured end; and
wherein the step of forming portions of the faceplate peripheral end formable material until the faceplate substantially matches the faceplate profile for the user's face thereby creating a faceplate customized contoured end includes the step of adding an addable material to the faceplate peripheral end.

* * * * *